(12) United States Patent
Kothakonda et al.

(10) Patent No.: US 8,883,795 B2
(45) Date of Patent: Nov. 11, 2014

(54) POLYMORPHIC FORMS OF RIFAXIMIN

(75) Inventors: Kiran Kumar Kothakonda, Brantford (CA); Allan W. Rey, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 35 days.

(21) Appl. No.: 13/704,938

(22) PCT Filed: Jun. 16, 2011

(86) PCT No.: PCT/CA2011/000690
§ 371 (c)(1),
(2), (4) Date: Dec. 17, 2012

(87) PCT Pub. No.: WO2011/156897
PCT Pub. Date: Dec. 22, 2011

(65) Prior Publication Data
US 2013/0090348 A1    Apr. 11, 2013

Related U.S. Application Data

(60) Provisional application No. 61/355,386, filed on Jun. 16, 2010.

(51) Int. Cl.
C07D 498/22    (2006.01)
A61K 31/395    (2006.01)
A61K 31/437    (2006.01)
C07D 498/18    (2006.01)

(52) U.S. Cl.
CPC ............ *C07D 498/18* (2013.01); *C07D 498/22* (2013.01)
USPC ...................... 514/254.11; 540/457

(58) Field of Classification Search
CPC ... C07D 498/22; A61K 31/395; A61K 31/437
USPC ...................... 540/457; 514/254.11
See application file for complete search history.

(56) References Cited

U.S. PATENT DOCUMENTS

| | | | |
|---|---|---|---|
| 7,709,634 B2 * | 5/2010 | Kothakonda et al. | 540/456 |
| 7,906,542 B2 * | 3/2011 | Viscomi et al. | 514/393 |
| 7,915,275 B2 * | 3/2011 | Viscomi et al. | 514/279 |
| 7,923,553 B2 * | 4/2011 | Viscomi et al. | 540/456 |
| 8,193,196 B2 * | 6/2012 | Viscomi et al. | 514/254.11 |
| 8,486,956 B2 * | 7/2013 | Gushurst et al. | 514/279 |
| 8,633,234 B2 * | 1/2014 | Rao et al. | 514/393 |

* cited by examiner

*Primary Examiner* — Bruck Kifle

(57) ABSTRACT

Provided for in the instant application are two additional polymorphic forms of rifaximin; namely substantially pure APO-I and APO-II. Also provided are processes for preparing substantially pure APO-I and APO-II. Rifaximin is a non-aminoglycoside antibiotic that has previously been found to be useful for the treatment of traveller's diarrhea caused by *Escherichia coli* bacteria, as well as in the treatment of irritable bowel syndrome, diverticular disease, hepatic encephalopathy, pyogenic skin infections and as an antibacterial prophylactic prior to colon surgery.

19 Claims, 4 Drawing Sheets

POLYMORPHIC FORMS OF RIFAXIMIN

TECHNICAL FIELD

The present invention relates to polymorphic forms of Rifaximin and to methods for their preparation.

BACKGROUND

Rifaximin (1) is a non-aminoglycoside semi-synthetic, nonsystemic antibiotic derived from Rifamycin, useful for the treatment of traveler's diarrhea in adults and in children 12 years of age and older caused by *Escherichia coli* bacteria. Rifaximin has also been evaluated for the treatment of irritable bowel syndrome, diverticular disease, hepatic encephalopathy, pyogenic skin infections, and as an antibacterial prophylactic prior to colon surgery. Chemically, Rifaximin is (2S, 16Z, 18E, 20S, 21S, 22R, 23R, 24R, 25S, 26S, 27S, 28E)-5,6,21,23,25-pentahydroxy-27-methoxy-2,4,11,16,20, 22,24,26-octamethyl-2,7-(epoxypentadeca-[1,11,13]trienimino)-benzofuro[4,5-e]-pyrido[1,2-(alpha)]-benzimidazole-1, 15(2H)dione, 25-acetate.

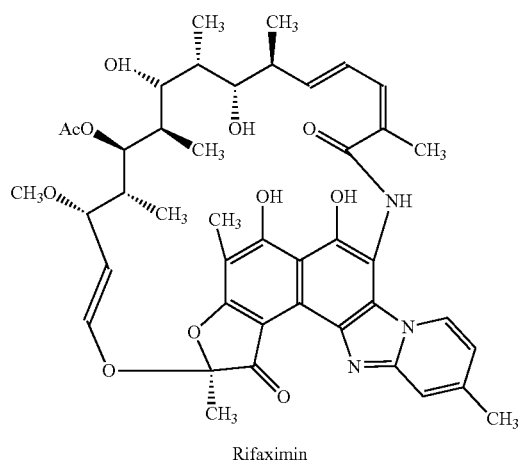

Rifaximin (1)

Rifaximin is currently sold in the US under the brand name Xifaxan™ by Salix Pharmaceuticals. It is also sold in Europe under the names Spiraxin™ Zaxine™, Normix™ and Rifacol™ and in India under the name Rifagut™.

U.S. Pat. No. 4,557,866 describes a new process for the synthesis of pyrido-imidazo-rifamycins of formula I. The process comprises reacting the rifamycin O with 4-methyl-2-aminopyridine.

U.S. Pat. No. 7,045,620, U.S. Pat. No. 7,612,199, US 20080262220 and US 20080262232 disclose crystalline polymorphous forms of Rifaximin (INN) antibiotic named Rifaximin alpha and Rifaximin beta, and a poorly crystalline form named Rifaximin gamma. These forms can be obtained by means of a crystallization process carried out by hot-dissolving the raw Rifaximin in ethyl alcohol and by causing the crystallization of the product by the addition of water at a determinate temperature and for a determinate time period. The crystallization is followed by drying carried out under controlled conditions until specific water content is reached in the end product in order to consistently obtain the above mentioned homogeneous polymorphic forms of Rifaximin.

US20080262024 describes forms of Rifaximin (INN) antibiotic, such as the poorly crystalline form named Rifaximin gamma, along with the production of medicinal preparations containing Rifaximin for oral and topical use.

US 20050272754 relates to Rifaximin polymorphic forms alpha, beta and gamma, the processes for their preparation and the use thereof in the manufacture of medicinal preparations for the oral or topical route.

WO 2008155728 describes a process which enables Rifaximin in a completely amorphous form to be obtained. Said process comprises the steps of dissolving crude Rifaximin in absolute ethanol while hot and then collecting after precipitation by cooling the title compound in amorphous form.

US 20090312357 discloses amorphous Rifaximin, methods of making it, and pharmaceutical compositions containing it. Also described are methods of converting amorphous Rifaximin to crystalline Rifaximin and vice versa.

WO 2009108730 relates to Rifaximin polymorphic, salt, hydrate, and amorphous forms, to their use in medicinal preparations and to therapeutic methods using them. Form zeta, Form eta, Form alpha-dry, Form i, Form beta-1, Form beta-2, Form epsilon-dry, and amorphous forms of Rifaximin as wells a mesylate salt are described.

US 20090082558 describes a stable amorphous form of Rifaximin. This form is chemically and polymorphic stable on storage and can be prepared by dissolving Rifaximin in a solvent to form a solution which is precipitated by adding an anti-solvent and isolating of the precipitated amorphous Rifaximin as an end product.

US 20090130201 describes crystalline polymorphous forms of Rifaximin (INN) antibiotic named Rifaximin delta and Rifaximin epsilon useful in the production of medicinal preparations containing Rifaximin for oral and topical use and obtained by means of a crystallization process carried out by hot-dissolving the raw Rifaximin in ethyl alcohol and by causing the crystallization of the product by addition of water at a determinate temperature and for a determinate time period, followed by drying carried out under controlled conditions until reaching a settled water content in the end product.

US 20100010028 describes polyols which stabilize polymorphous forms of Rifaximin, in particular the beta form. When polyols having at least two hydroxyl groups are added to Rifaximin powder, polymorph beta is stable and remains stable in time independently from the environment humidity. A method to prepare formulations constituted by pure and stable polymorphous forms able to give a pharmaceutical product is also described.

SUMMARY

The present invention relates to crystalline forms of Rifaximin, namely polymorphic forms of Rifaximin termed herein as APO-I and APO-II and to processes for preparing APO-I and APO-II in substantially pure form.

Illustrative embodiments of the present invention provide substantially pure polymorphic form APO-I of Rifaximin.

Illustrative embodiments of the present invention provide the polymorphic form APO-I of Rifaximin described herein having a PXRD diffractogram comprising peaks, in terms of degrees 2-theta, at approximately 6.32, 6.70, 8.36, 9.57, 12.67 and 18.73

Illustrative embodiments of the present invention provide the polymorphic form APO-I of Rifaximin described herein having a PXRD diffractogram comprising peaks, in terms of degrees 2-theta, at approximately 6.32, 6.52, 6.54, 6.70, 8.36, 8.38, 9.57, 12.67, 12.68, 18.73 and 24.94.

Illustrative embodiments of the present invention provide the polymorphic form APO-I of Rifaximin described herein having a PXRD diffractogram substantially similar to the PXRD diffractogram as depicted in FIG. 1.

Illustrative embodiments of the present invention provide the polymorphic form APO-I of Rifaximin described herein having a PXRD diffractogram as depicted in FIG. 1.

Illustrative embodiments of the present invention provide the polymorphic form APO-I of Rifaximin described herein having a 1% KBr FTIR spectrum comprising peaks, in terms of $cm^{-1}$, at approximately 3427.9, 2968.1, 2934.1, 1714.2 1647.7, 1587.3, 1507.1, 1373.7, 1338.1, 1226.4, 1157.0, and 1124.1.

Illustrative embodiments of the present invention provide the polymorphic form APO-I of Rifaximin described herein having a 1% KBr FTIR spectrum comprising peaks, in terms of $cm^{-1}$, at approximately 2968.1, 2934.1, 1714.2, 1507.1, and 1124.1.

Illustrative embodiments of the present invention provide the polymorphic form APO-I of Rifaximin described herein having a FTIR spectrum substantially similar to the FTIR spectrum as depicted in FIG. 2.

Illustrative embodiments of the present invention provide the polymorphic form APO-I of Rifaximin described herein having a FTIR spectrum as depicted in FIG. 2.

Illustrative embodiments of the present invention provide a pharmaceutical formulation comprising the polymorphic form APO-I of Rifaximin described herein and a pharmaceutically acceptable excipient.

Illustrative embodiments of the present invention provide a process for preparation of a polymorphic form APO-I of Rifaximin comprising: dissolving Rifaximin in a first organic solvent thereby forming a Rifaximin solution; adding the Rifaximin solution to a second organic solvent thereby forming a mixture; stirring the mixture; heating the mixture to a temperature of about 40° C. to about 50° C.; isolating the polymorphic form APO-I of Rifaximin; and drying the polymorphic form APO-I of Rifaximin in a vacuum oven at a temperature of about 5° C. to about 90° C.

Illustrative embodiments of the present invention provide a process for preparation of a substantially pure polymorphic form APO-I of Rifaximin described herein wherein the stirring occurs for a time period of from about 8 hours to about 12 hours.

Illustrative embodiments of the present invention provide a process for preparation of a polymorphic form APO-I of Rifaximin described herein wherein the first organic solvent is a $C_3$ to $C_7$ alkyl acetate.

Illustrative embodiments of the present invention provide a process for preparation of a polymorphic form APO-I of Rifaximin described herein wherein the first organic solvent is ethyl acetate.

Illustrative embodiments of the present invention provide a process for preparation of a polymorphic form APO-I of Rifaximin described herein wherein the temperature for drying temperature is from about 40° C. to about 60° C.

Illustrative embodiments of the present invention provide a process for preparation of a polymorphic form APO-I of Rifaximin described herein wherein the second organic solvent is a $C_6$ to $C_9$ hydrocarbon.

Illustrative embodiments of the present invention provide a process for preparation of a polymorphic form APO-I of Rifaximin described herein wherein the second organic solvent is heptanes.

Illustrative embodiments of the present invention provide a substantially pure polymorphic form APO-II of Rifaximin.

Illustrative embodiments of the present invention provide the polymorphic form APO-II of Rifaximin described herein having a PXRD diffractogram comprising peaks, in terms of degrees 2theta, at approximately 6.18, 6.33, 6.93, 8.90, 14.34, 19.42, 20.63, and 26.49.

Illustrative embodiments of the present invention provide the polymorphic form APO-II of Rifaximin described herein having a PXRD diffractogram comprising peaks, in terms of degrees 2theta, at approximately 6.18, 6.19, 6.33, 6.34, 6.93, 6.94, 8.90, 8.92, 14.34, 17.07, 19.42, 19.85, 20.63, 21.33, 26.26, and 26.49.

Illustrative embodiments of the present invention provide the polymorphic form APO-II of Rifaximin described herein having a PXRD diffractogram substantially similar to the PXRD diffractogram as depicted in FIG. 3.

Illustrative embodiments of the present invention provide the polymorphic form APO-II of Rifaximin described herein having a PXRD diffractogram as depicted in FIG. 3.

Illustrative embodiments of the present invention provide the polymorphic form APO-II of Rifaximin described herein having a 1% KBr FTIR spectrum comprising peaks, in terms of $cm^{-1}$, at approximately 3428.3, 2971.8, 2934.0, 1720.7, 1646.2, 1588.2, 1504.9, 1374.0, 1320.8, 1226.7, and 1120.2.

Illustrative embodiments of the present invention provide the polymorphic form APO-II of Rifaximin described herein having a 1% KBr FTIR spectrum comprising peaks, in terms of $cm^{-1}$, at approximately 2971.8, 1720.7, 1504.9, and 1120.2.

Illustrative embodiments of the present invention provide the polymorphic form APO-II of Rifaximin described herein having a FTIR spectrum substantially similar to the FTIR spectrum as depicted in FIG. 4.

Illustrative embodiments of the present invention provide the polymorphic form APO-II of Rifaximin described herein having a FTIR spectrum as depicted in FIG. 4.

Illustrative embodiments of the present invention provide a pharmaceutical formulation comprising the polymorphic form APO-II of Rifaximin described herein and pharmaceutically acceptable excipients.

Illustrative embodiments of the present invention provide a process for preparation of a substantially pure polymorphic form APO-II of Rifaximin comprising: dissolving Rifaximin in a third organic solvent thereby forming a Rifaximin solution; adding the Rifaximin solution to a fourth organic solvent thereby forming a mixture; stirring the mixture; heating the mixture to a temperature of from about 40° C. to about 50° C.; isolating the polymorphic form APO-II of Rifaximin; and drying the polymorphic form APO-II of Rifaximin in a vacuum oven at a temperature of about 5° C. to about 90° C.

Illustrative embodiments of the present invention provide a process for preparation of a polymorphic form APO-II of Rifaximin described herein wherein the third organic solvent is ethyl acetate.

APO-I and APO-II polymorphic forms may have properties suitable for commercial use. These may include properties such as chemical stability, polymorphic stability, and/or varying solubilities relative to other forms of Rifaximin.

Other aspects and features of the present invention will become apparent to those ordinarily skilled in the art upon review of the following description of specific embodiments of the invention with the accompanying Figures.

BRIEF DESCRIPTION OF THE DRAWINGS

Drawings which illustrate embodiments of the invention are.

DETAILED DESCRIPTION

Figure 1:
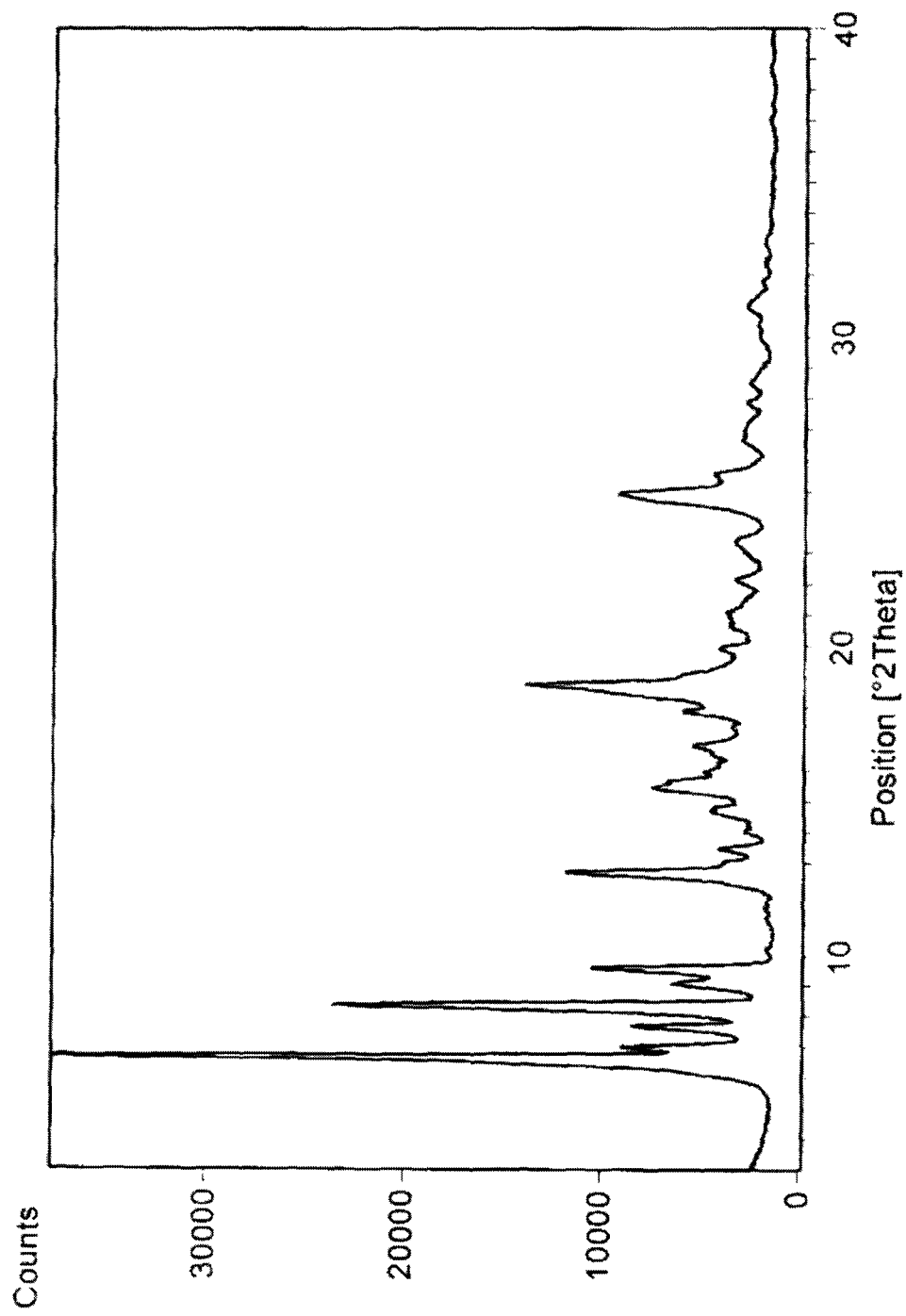
FIG. 1: is a powder X-ray diffraction (PXRD) diffractogram of APO-I

As used herein, the term "substantially pure", when used in reference to a polymorphic form, means that the polymorphic form has a polymorphic purity of 90% or more. Often the polymorphic purity will be 95% or more. Often the polymorphic purity will be 99% or more.

When used in reference to a diffractogram, a spectrum and/or data presented in a graph, the term "substantially similar" means that the subject diffractogram, spectrum and/or data presented in a graph encompasses all diffractograms, spectra and/or data presented in graphs that vary within acceptable boundaries of experimentation that are known to a person of skill in the art. Such boundaries of experimentation will vary depending on the type of the subject diffractogram, spectrum and/or data presented in a graph, but will nevertheless be known to a person of skill in the art.

When used in reference to a peak in a PXRD diffractogram, the term "approximately" means that the peak may vary by ±0.2 degrees 2-theta of the subject value.

When used in reference to a peak in a FTIR spectrum, the term "approximately" means that the peak may vary by ±5 $cm^{-1}$ of the subject value.

As used herein when referring to a diffractogram, spectrum and/or to data presented in a graph, the term "peak" refers to a feature that one skilled in the art would recognize as not attributing to background noise.

Depending on the nature of the methodology applied and the scale selected to display results obtained from an X-ray diffraction analysis, an intensity of a peak obtained may vary quite dramatically. For example, it is possible to obtain a relative peak intensity of 0.001% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

Processes for the preparation of Rifaximin often provide a polymorphic form that has unsuitable bioavailability and/or a mixture of polymorphic forms.

The transformation of particular polymorphic forms of Rifaximin to other polymorphic forms is known (for instance, G. C. Viscomi et al., CrystEngComm, 2008, 10, 1074-1081). The present invention provides stable polymorphic forms and methods that may be used to consistently prepare these polymorphic forms in a pure form.

In an illustrative embodiment, the present invention comprises a crystalline form of Rifaximin which is referred to herein as APO-I. APO-I may be characterized by an X-ray powder diffraction pattern comprising peaks, in terms of 2-theta, at approximately 6.32±0.2, 6.52±0.2, 6.54±0.2, 6.70±0.2, 8.36±0.2, 8.38±0.2, 9.57±0.2, 12.67±0.2, 12.68±0.2, 18.73±0.2 and 24.94±0.2. An illustrative PXRD diffractogram of APO-I is given in FIG. 1.

Illustrative relative peak intensities of the aforementioned peaks appearing in a typical PXRD for APO-I, expressed in terms of percent, are illustrated below in Table 1.

TABLE 1

Relative peak intensities for APO-I

| Angle 2-theta | Relative intensity % |
|---|---|
| 6.32 | 19.41 |
| 6.52 | 44.07 |
| 6.54 | 22.04 |
| 6.70 | 100.00 |
| 8.36 | 59.42 |
| 8.38 | 29.71 |
| 9.57 | 25.22 |
| 12.67 | 26.41 |
| 12.68 | 25.91 |
| 18.73 | 30.48 |
| 24.94 | 21.46 |

Figure 2:
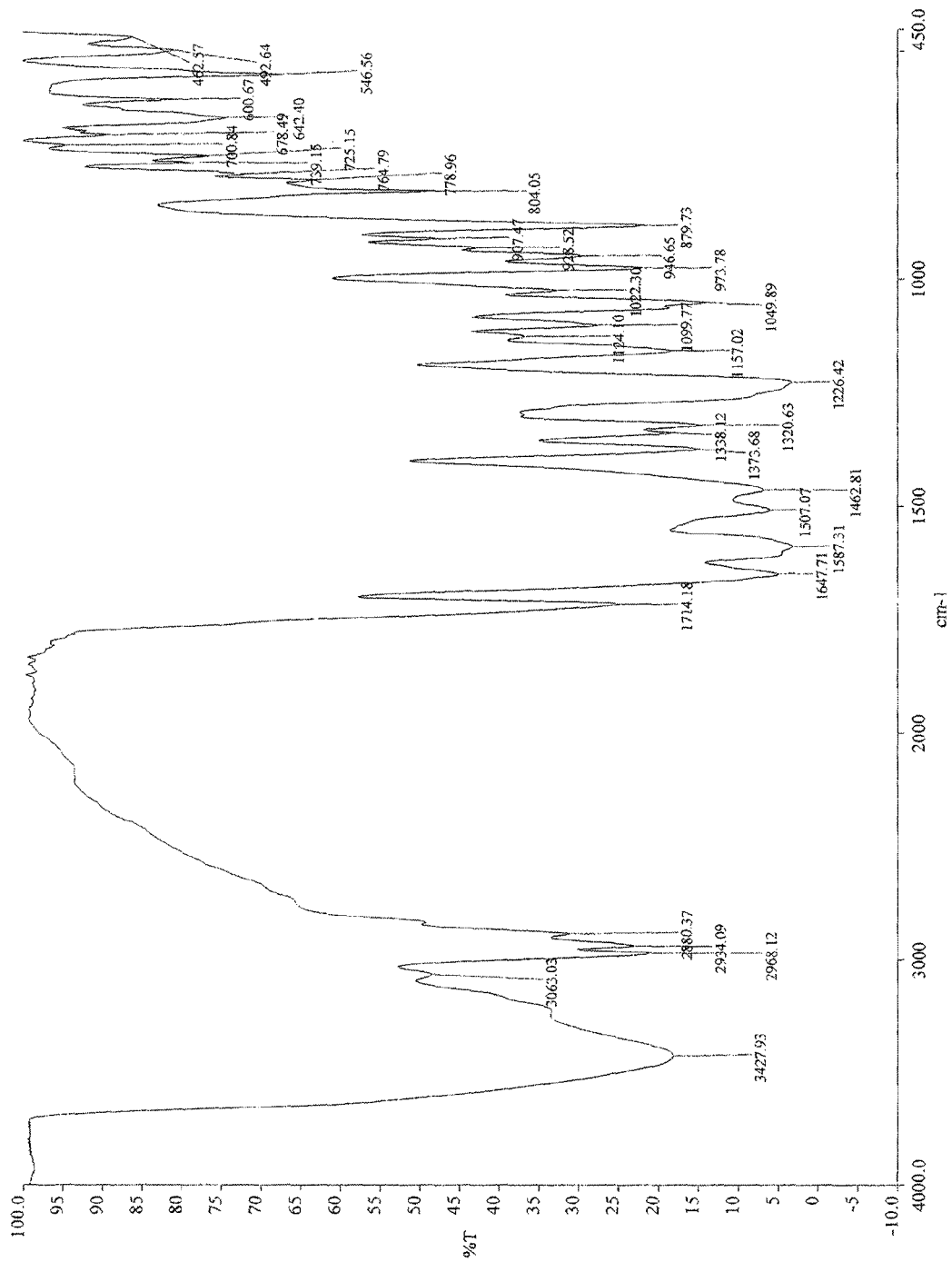
FIG. 2: is a Fourier Transform Infrared (FTIR) spectrum of APO-I.

An illustrative FTIR spectrum of APO-I according to the conditions given Example 1 is shown in FIG. 2. APO-I Rifaximin may have an absorption band ("peak") at any one or more of the values expressed in $cm^{-1}$ given in Table 2. Some illustrative and non limiting possible observations regarding peak intensity (% transmission) of the peaks are also set out in Table 2.

TABLE 2

Form APO-I Rifaximin

| Peak ($cm^{-1}$) | Intensity (% Transmission) |
|---|---|
| 3427.9 | 18.1 |
| 2968.1 | 21.2 |
| 2934.1 | 23.1 |
| 1714.2 | 24.9 |
| 1647.7 | 4.9 |
| 1587.3 | 3.2 |
| 1507.1 | 6.0 |
| 1373.7 | 15.2 |
| 1338.1 | 18.4 |
| 1226.4 | 3.3 |
| 1157.0 | 18.5 |
| 1124.1 | 36.8 |

In another illustrative embodiment, the present invention provides a process of preparing APO-I comprising:

a. dissolving Rifaximin in a first organic solvent thereby forming a Rifaximin solution;

b. adding the Rifaximin solution to a second organic solvent thereby forming a mixture;

c. stirring the mixture;

d. heating the mixture to a temperature of from about 40° C. to 50° C.;

e. stirring the mixture for a time period of from about 2 hours to about 6 hours;

f. isolating the APO-I; and g. drying the APO-I in vacuum at a temperature of about 5° C. to about 90° C.

The first organic solvent may be a $C_3$ to $C_7$ alkyl acetate, for example ethyl acetate. The second organic solvent may be a $C_6$ to $C_9$ cyclic alkyl hydrocarbon or a $C_6$ to $C_g$ acyclic alkyl hydrocarbon, for example heptanes. The stirring may occur for a time period of from about 8 hours to about 12 hours.

In an illustrative embodiment, the present invention comprises a form of Rifaximin which is referred to herein as APO-II. APO-II may be characterized by an X-ray powder diffraction pattern comprising peaks, in terms of 2-theta, at approximately 6.18±0.2, 6.19±0.2, 6.33±0.2, 6.34±0.2, 6.93±0.2, 6.94±0.2, 8.90±0.2, 8.92±0.2, 14.34±0.2, 17.07±0.2, 19.42±0.2, 19.85±0.2, 20.63±0.2, 21.33±0.2, 26.26±0.2, and 26.49±0.2. An illustrative PXRD diffractogram of APO-II is given in FIG. 3.

Illustrative relative peak intensities of the aforementioned peaks appearing in a typical PXRD for APO-II, expressed in terms of percent, are illustrated below in Table 3.

TABLE 3

Relative peak intensities for APO-II

| Angle 2θ | Relative intensity % |
|---|---|
| 6.18 | 44.91 |
| 6.19 | 22.46 |
| 6.33 | 100.00 |
| 6.34 | 50.00 |
| 6.93 | 54.39 |
| 6.94 | 27.19 |
| 8.90 | 36.16 |
| 8.92 | 18.08 |
| 14.34 | 21.86 |
| 17.07 | 15.77 |
| 19.42 | 20.58 |
| 19.85 | 12.05 |
| 20.63 | 15.77 |
| 21.33 | 12.97 |
| 26.26 | 13.15 |
| 26.49 | 15.35 |

Figure 4:
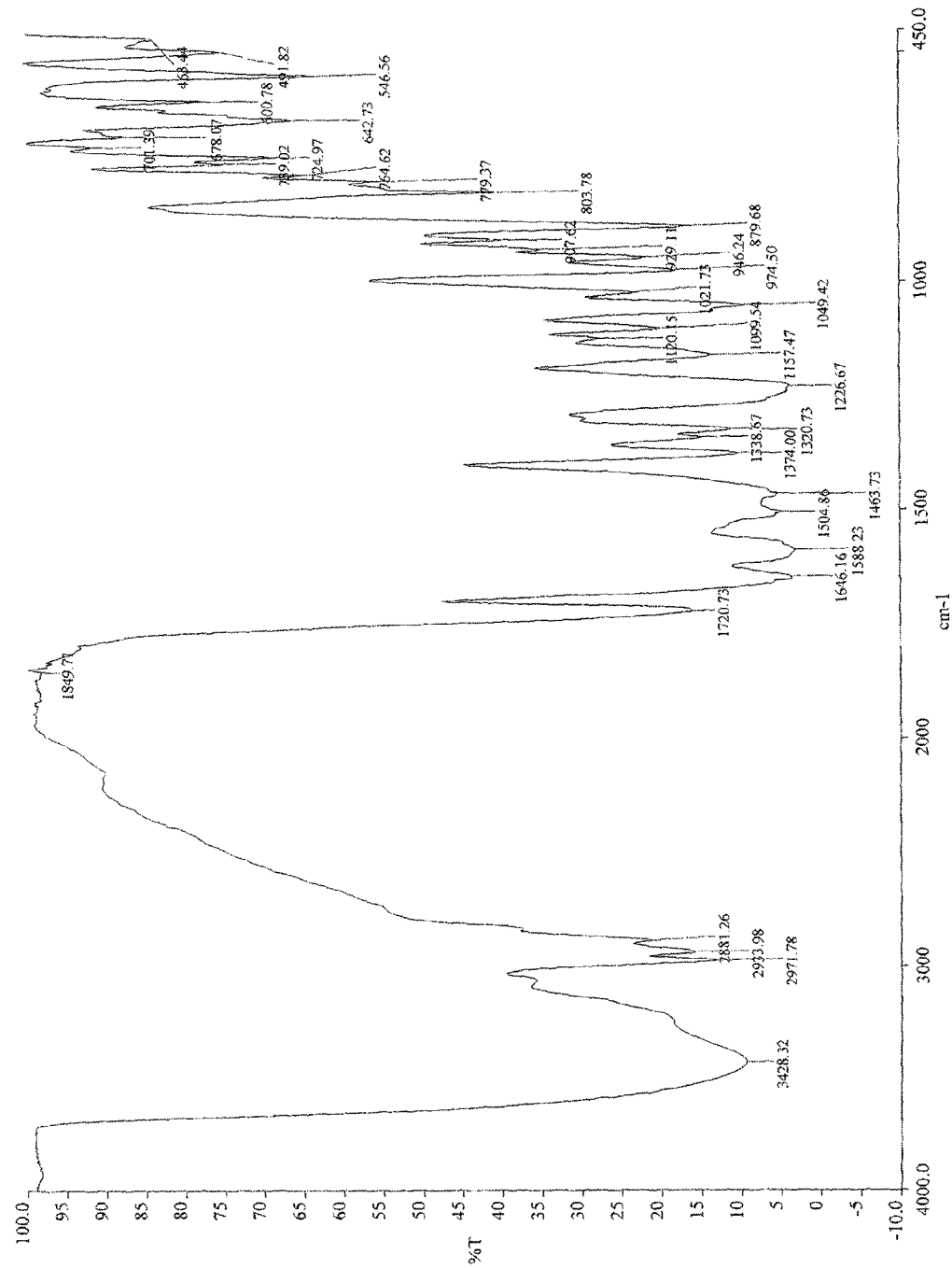
FIG. 4: is a Fourier Transform Infrared (FTIR) spectrum of APO-II

An illustrative FTIR spectrum of Form APO-II according to the conditions given Example 2 is shown in FIG. 4. APO-II Rifaximin may have an absorption band ("peak") at any one or more of the values expressed in $cm^{-1}$ given in Table 4. Some illustrative and non limiting possible observations regarding peak intensity (% transmission) of the peaks are also set out in Table 4.

TABLE 4

Form APO-II Rifaximin

| Peak ($cm^{-1}$) | Intensity (% Transmission) |
|---|---|
| 3428.3 | 9.4 |
| 2971.8 | 13.2 |
| 2934.0 | 15.8 |
| 1720.7 | 16.2 |
| 1646.2 | 3.6 |
| 1588.2 | 3.2 |
| 1504.9 | 4.9 |
| 1374.0 | 10.3 |
| 1320.8 | 11.2 |
| 1226.7 | 3.8 |
| 1120.2 | 27.9 |

In another illustrative embodiment, the present invention provides a process of preparing APO-II comprising:

A. dissolving Rifaximin in a third organic solvent thereby forming a Rifaximin solution;
B. adding the Rifaximin solution to a fourth organic solvent thereby forming a mixture;
C. stirring the mixture;
D. heating the mixture to a temperature of from about 40° C. to about 50° C.;
E. isolating APO-II by filtration; and
F. drying the APO-II in vacuum at a temperature of from about 5° C. to about 90° C.

APO-I and APO-II may be formulated into pharmaceutical formulations, typically by adding at least one pharmaceutically acceptable excipient and by using techniques well understood by a person of skill in the art. Many techniques known to one of skill in the art and many pharmaceutically acceptable excipients known to one of skill in the art are described in *Remington: the Science & Practice of Pharmacy* by Alfonso Gennaro, 20th ed., Lippencott Williams & Wilkins, (2000).

The following examples are illustrative of some of the embodiments of the invention described herein. These examples do not limit the spirit or scope of the invention in any way

EXAMPLES

Powder X-Ray Diffraction Analysis: The data were acquired on a PANanalytical X-Pert Pro MPD diffractometer with fixed divergence slits and an X-Celerator RTMS detector. The diffractometer was configured in Bragg-Brentano geometry; data was collected over a 2-theta range of 3 to 40 using CuKα radiation at a power of 40 mA and 45 kV. CuKβ radiation was removed using a divergent beam nickel filter. A step size of 0.017 degrees was used. A step time of 50 seconds was used. Samples were rotated at 1 Hz to reduce preferred orientation effects. The samples were prepared by the back-loading technique.

Fourier Transform Infrared (FTIR) Analysis: The FTIR spectrum was collected at 4 $cm^{-1}$ resolution using a Perkin Elmer Paragon 1100 single beam FTIR instrument. The samples were intimately mixed in an approximately 1:100 ratio (w/w) with potassium bromide using an agate mortar and pestle to a fine consistency; the mixture was compressed in a pellet die at a pressure of 4 to 6 tonnes for a time period between 2 and 5 minutes. The resulting disk was scanned 4 times versus a collected background. Data was baseline corrected and normalized Example 1

Preparation of Form APO-I Rifaximin

Rifaximin (130 g) was dissolved in ethyl acetate (390 mL) followed by adding this solution to heptanes (650 mL). After stirring at room temperature for 12 hrs, the resulting suspension was heated to 45° C. and stirred for 4 hrs to obtain a uniform mixture. The suspension was filtered, washed with water (260 mL) and dried in a vacuum oven at 50° C. to provide Form APO-I Rifaximin (127 g).

Example 2

Preparation of Form APO-II Rifaximin

Rifaximin (50 g) was dissolved in ethyl acetate (150 mL) followed by adding this solution to heptanes (250 mL) at room temperature. After stirring at room temperature for 21 hrs, the resulting suspension was heated to 45° C. and stirred for 6 hrs to obtain a uniform mixture. The suspension was filtered, and dried in a vacuum oven at 60° C. to provide Form APO-II Rifaximin (44 g).

What is claimed is:

1. A polymorphic form of Rifaximin having a PXRD diffractogram comprising peaks, in terms of degrees 2-theta, at approximately 6.32, 6.70, 8.36, 9.57, 12.67 and 18.73.

2. The polymorphic form of Rifaximin of claim 1 further comprising peaks, in terms of degrees 2-theta, at approximately 6.52, 6.54, 8.38, 12.68, and 24.94.

3. The polymorphic form of Rifaximin of claim 1 having a PXRD diffractogram as depicted in FIG. 1.

4. The polymorphic form of Rifaximin of claim 1 having a 1% KBr FTIR spectrum comprising peaks, in terms of $cm^{-1}$, at approximately 3427.9, 2968.1, 2934.1, 1714.2 1647.7, 1587.3, 1507.1, 1373.7, 1338.1, 1226.4, 1157.0, and 1124.1.

5. The polymorphic form of Rifaximin of claim 1 having a FTIR spectrum as depicted in FIG. 2.

6. A pharmaceutical formulation comprising the polymorphic form of Rifaximin of claim 1 and a pharmaceutically acceptable excipient.

7. A process for preparation of the polymorphic form of Rifaximin of claim 1, the process comprising:
    dissolving Rifaximin in a first organic solvent selected from the group consisting of C3 to C7 alkyl acetates, thereby forming a Rifaximin solution;
    adding the Rifaximin solution to a second organic solvent selected from the group consisting of $C_6$ to $C_9$ hydrocarbons, thereby forming a mixture;
    stirring the mixture;
    heating the mixture to a temperature of about 40° C. to about 50° C.;
    isolating the polymorphic form of Rifaximin; and
    drying the polymorphic form of Rifaximin in a vacuum oven at a temperature of about 5° C. to about 90° C.

8. The process of claim 7 wherein the stirring occurs for a time period of from about 8 hours to about 12 hours.

9. The process of claim 7 wherein the first organic solvent is ethyl acetate.

10. The process of claim 7 wherein the temperature for drying temperature is from about 40° C. to about 60° C.

11. The process of claim 7 wherein the second organic solvent is heptanes.

12. A polymorphic form of Rifaximin having a PXRD diffractogram comprising peaks, in terms of degrees 2-theta, at approximately 6.18, 6.33, 6.93, 8.90, 14.34, 19.42, 20.63, and 26.49.

13. The polymorphic form of Rifaximin of claim 12 further comprising peaks, in terms of degrees 2-theta, at approximately 6.19, 6.34, 6.94, 8.92, 17.07, 19.85, 21.33, and 26.26.

Figure 3:
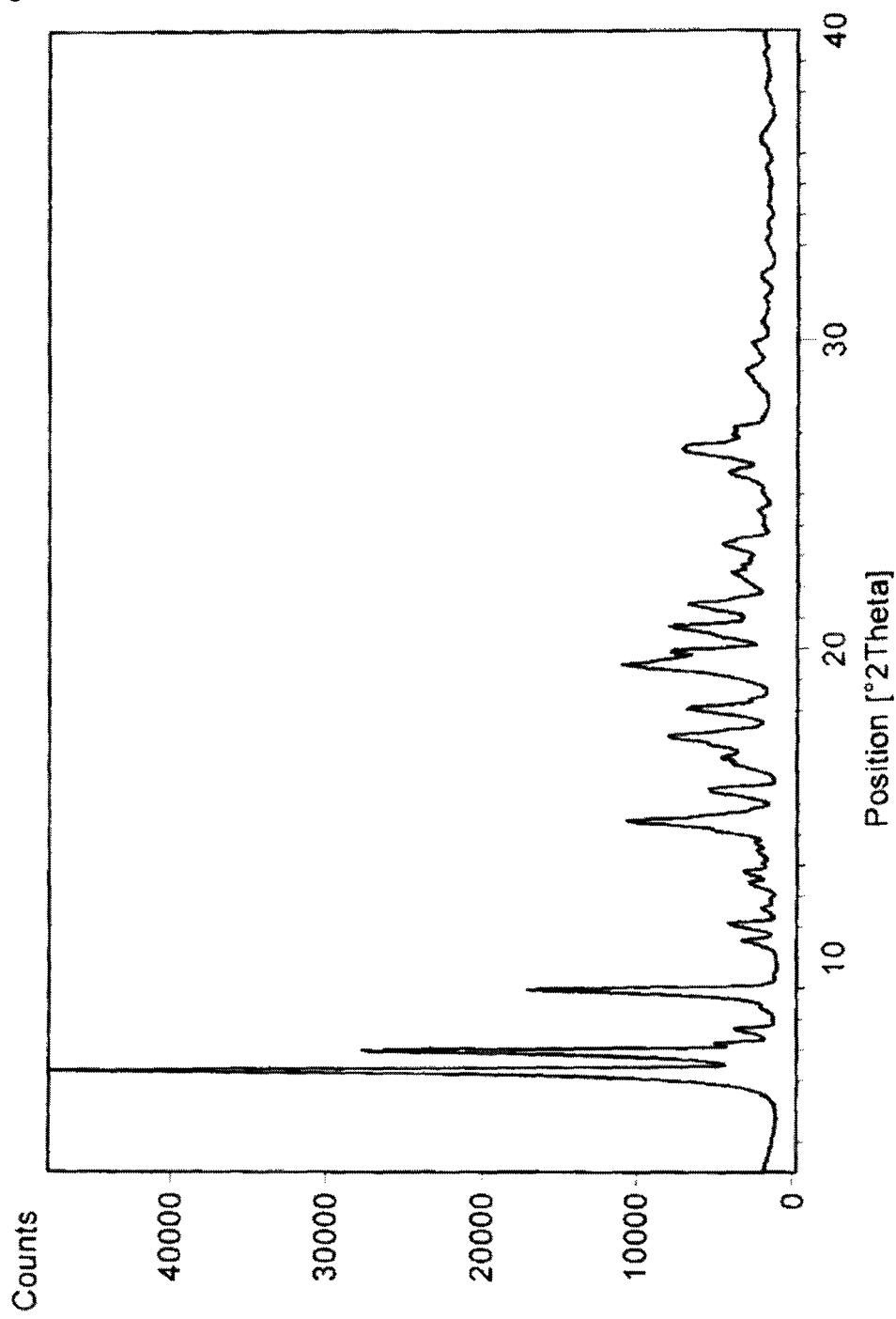
FIG. 3: is a powder X-ray diffraction (PXRD) diffractogram of APO-II

14. The polymorphic form of Rifaximin of claim 12 having a PXRD diffractogram as depicted in FIG. 3.

15. The polymorphic form of Rifaximin of claim 12 having a 1% KBr FTIR spectrum comprising peaks, in terms of $cm^{-1}$, at approximately 3428.3, 2971.8, 2934.0, 1720.7, 1646.2, 1588.2, 1504.9, 1374.0, 1320.8, 1226.7, and 1120.2.

16. The polymorphic form of Rifaximin of claim 12 having a FTIR spectrum as depicted in FIG. 4.

17. A pharmaceutical formulation comprising the polymorphic form of Rifaximin of claim 12 and pharmaceutically acceptable excipients.

18. A process for preparation of the polymorphic form of Rifaximin of claim 12, the process comprising:
    dissolving Rifaximin in a third organic solvent selected from the group consisting of C3 to C7 alkyl acetates, thereby forming a Rifaximin solution;
    adding the Rifaximin solution to a fourth organic solvent selected from the group consisting of C6 to C9 hydrocarbons, thereby forming a mixture;
    stirring the mixture;
    heating the mixture to a temperature of from about 40° C. to about 50° C.;
    isolating the polymorphic form of Rifaximin; and
    drying the polymorphic form of Rifaximin in a vacuum oven at a temperature of about 5° C. to about 90° C.

19. The process of claim 18 wherein the third organic solvent is ethyl acetate.

* * * * *